United States Patent [19]

Johnson et al.

[11] 4,011,058
[45] Mar. 8, 1977

[54] PRODUCTION OF SUBSTITUTE NATURAL GAS FROM GASIFICATION OF COAL CHAR

[75] Inventors: Marvin M. Johnson; Donald C. Tabler; Gerhard P. Nowack, all of Bartlesville, Okla.

[73] Assignee: Phillips Petroleum Company, Bartlesville, Okla.

[22] Filed: Oct. 1, 1975

[21] Appl. No.: 618,719

[52] U.S. Cl. .............................. 48/197 R; 48/210; 252/373; 260/449 M; 423/246
[51] Int. Cl.[2] ...................... C10J 3/00; C10K 3/00
[58] Field of Search .................. 48/197 R, 210, 211, 48/212, 213; 252/373, 437, 470, 473; 260/449 M; 423/246

[56] References Cited

UNITED STATES PATENTS

| | | | |
|---|---|---|---|
| 2,519,284 | 8/1950 | Ray et al. ........................ | 423/246 |
| 3,298,966 | 1/1967 | Bagnetto .......................... | 252/437 |
| 3,600,145 | 8/1971 | Johnson et al. .................. | 48/197 R |
| 3,692,506 | 9/1972 | Johnson .......................... | 48/197 R |

Primary Examiner—Robert L. Lindsay, Jr.
Assistant Examiner—George C. Yeung

[57] ABSTRACT

A carbonaceous material is converted to a fuel gas which is fungible with natural gas by a combination of steps comprising gasifying the carbonaceous material in the presence of air and carbon dioxide, purifying the effluent stream and separating carbon monoxide therefrom, catalytically reacting steam with the separated carbon monoxide and recovering a methane-rich product gas.

21 Claims, 1 Drawing Figure

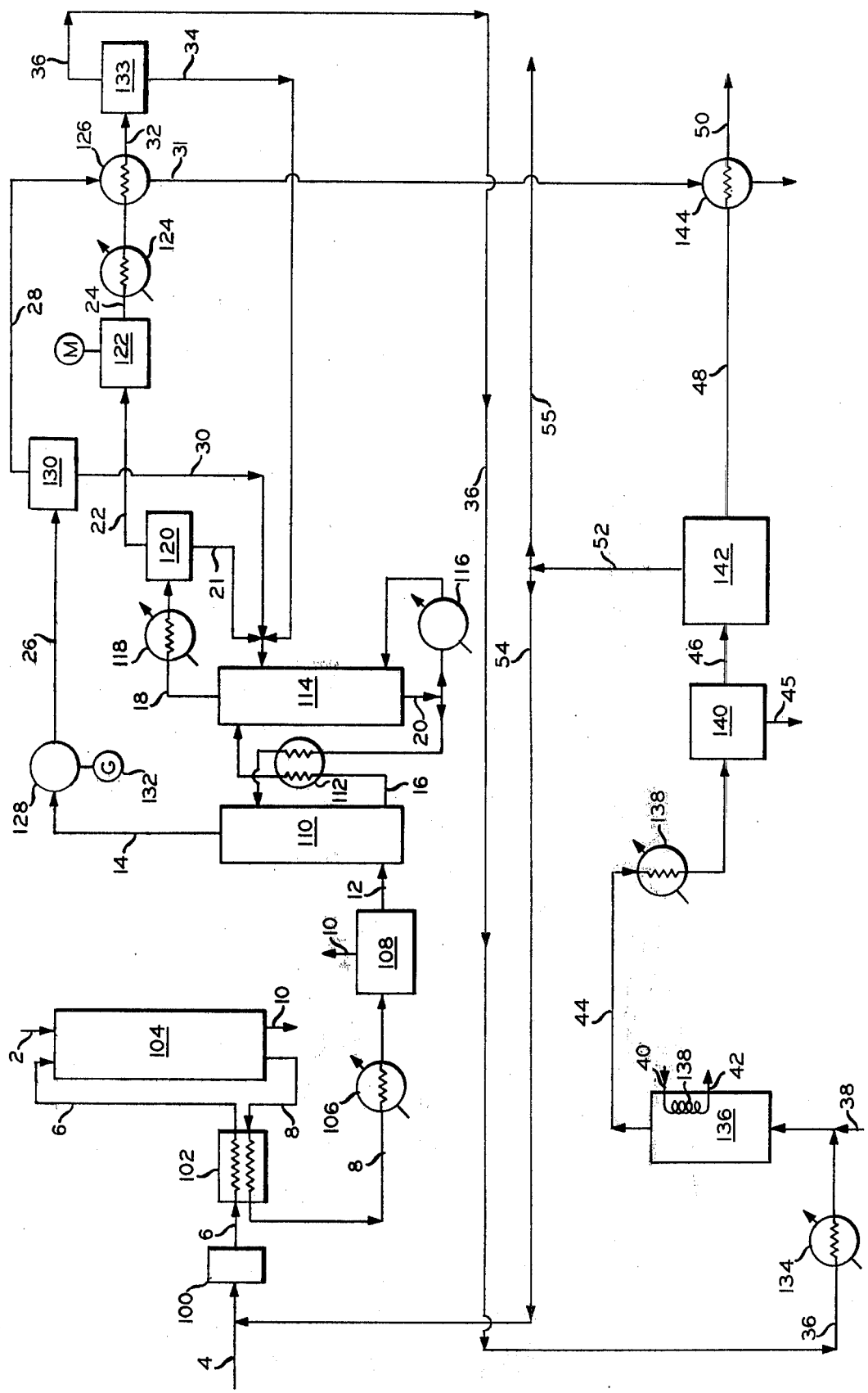

PRODUCTION OF SUBSTITUTE NATURAL GAS FROM GASIFICATION OF COAL CHAR

This invention relates to the production of fuel gas from a carbonaceous material which is interchangeable with natural gas.

The synthetic production of fuel gas is desirable to meet the supply for utility pipeline gas in those areas where the demand exceeds the supply, particularly during periods of peak load. Such pipeline gas should preferably be made from a cheap fuel. Additionally, the process by which the gas is made must be competitive with other energy sources.

It has been proposed in the past to gasify carbonaceous solids such as coal, lignite and the like in the presence of other gases to obtain more useful gases for further synthesis or as a source of high B.t.u. gas. It is well known that carbonaceous fuels react with hydrogen under pressure to produce methane gas. However, the cost of hydrogen required for the process can make the process prohibitively expensive. It is also known that carbonaceous fuels react with oxygen under proper conditions to produce carbon monoxide which can, by means of a methanation process, be converted catalytically to methane. The cost of pure oxygen required for the process can make the process prohibitively expensive. Air is generally not used as the source of oxygen due to the diluting effect of the nitrogen in the air and the problems generally encountered in separating the nitrogen from the various process streams.

Accordingly, it is an object of this invention to provide a process for the production of a fuel gas from a carbonaceous solid.

Other objects, aspects and advantages of the present invention will be readily apparent to those skilled in the art from a study of this disclosure, appended claims and the attached drawing which is a detailed schematic diagram of the process of the present invention.

In accordance with the present invention there is provided a process for the production of a product gas comprising methane, which comprises:

a. gasifying a carbonaceous material at an elevated temperature in the presence of air and carbon dioxide to produce a raw process stream comprising carbon monoxide, carbon dioxide and nitrogen, b. separating carbon monoxide from the raw process stream, and c. reacting the separated carbon monoxide in a catalytic methanation zone to produce an effluent gas stream comprising methane.

More particularly, in accordance with the present invention, there is provided a process for the production of a product gas comprising methane, which comprises, in combination, the steps of a. gasifying a carbonaceous material at an elevated temperature in the presence of air and carbon dioxide to produce a raw process stream comprising carbon monoxide, carbon dioxide and nitrogen;

b. cooling, cleaning and purifying the raw process stream to obtain a stream consisting essentially of carbon monoxide and nitrogen;

c. separating carbon monoxide from the stream consisting essentially of carbon monoxide and nitrogen;

d. combining steam with the separated carbon monoxide and reacting the resulting CO/steam mixture in a catalytic methanation zone to produce an effluent gas stream consisting essentially of carbon dioxide, methane and hydrogen; and e. cooling the effluent gas stream consisting essentially of carbon dioxide, methane and hydrogen and separating impurities therefrom to produce a product stream comprising methane.

While any carbonaceous material can be employed in the practice of this invention, the invention is particularly suitable for the conversion of materials such as low grade bituminous coal char, lignite char and petroleum coke. The char or coke can contain up to about 4 weight percent sulfur, on a moisture-free, ash-free basis. Thus, a variety of carbonaceous materials can be converted to char and used in the process.

The char is introduced into the gasification zone in the form of small particles, generally smaller than about 40 mesh. Within the gasification zone the char is reacted with oxygen and carbon dioxide according to the following reaction:

$$6C + 2O_2 + 3CO_2 + 7.52N_2 \rightarrow 8CO + CO_2 + 7.52N_2$$

Gasification of the char takes takes place at a temperature above 1800° F (about 980° C), preferably at about 2200° F (about 1200° C) at a pressure of about 300 psig (about 2.07 MPa). In view of the limited amount of oxygen available for reaction, part of the carbon reacts to form carbon monoxide and part reacts to form carbon dioxide. The carbon dioxide is present in excess. A part of it combines with a part of the carbon to form additional carbon monoxide. The remainder of the carbon dioxide acts to help regulate the temperature of the gasification reaction.

The several treatment and reaction zones, including the synthesis gas generator, i.e., the gasification zone, the gas purifying zones, the carbon monoxide separation and recovery zone and the methanation reactor are known in the art and are operated, unless otherwise indicated, at conventional conditions. Such zones and conditions will not be discussed herein in any detail.

In one embodiment of the present invention, the carbon monoxide separation and recovery operation is effected using a particular carbon monoxide absorbent system. Thus, in accordance with the one embodiment, the feedstream consisting essentially of carbon monoxide and nitrogen is introduced to the carbon monoxide removal and recovery zone wherein it is contacted with an absorbent system consisting essentially of an inert hydrocarbon diluent and at least one copper (I) salt of an organic sulfonic acid.

The copper (I) salts employed in the absorbent system are selected from the group consisting of:

a. the copper (I) salt of an alkane sulfonic acid having from 4 to 20 carbon atoms per molecule;

b. the copper (I) salt of an aromatic sulfonic acid, including hydroxyaromatic and haloaromatic sulfonic acids, having from 6 to 22 carbon atoms per molecule; and c. the copper (I) salt of a petroleum sulfonic acid.

The alkane sulfonic acids useful in the practice of this invention can be straight chain or branched. Examples of suitable alkane sulfonic acids include n-butanesulfonic acid, 2-ethylhexanesulfonic acid, 2-methylnonanesulfonic acid, dodecanesulfonic, acid, 2-ethyl-5-n-octyldecanesulfonic acid, n-eiconsanesulfonic acid and the like. A presently preferred alkane sulfonic acid is 2-ethylhexanesulfonic acid.

The aromatic, hydroxyaromatic and haloaromatic sulfonic acids useful in the practice of this invention include benzenesulfonic acid, alkylbenzenesulfonic acids wherein the alkyl member contains from 1 to 16 carbon atoms, such as p-toluenesulfonic acid, p-dodecylbenzenesulfonic acid, p-hexadecylbenzenesulfonic acid and the like, naphthalenesulfonic acids, phenolsulfonic acid, naphtholsulfonic acids, and halo-benzenesulfonic acids, such as p-chlorobenzenesulfonic acid, p-bromobenzenesulfonic acid, and the like. A presently preferred aromatic sulfonic acid is p-dodecylbenzenesulfonic acid. Commercially available mixtures of o-, m- and p-dodecylbenzenesulfonic acid can be employed. Preferably, the mixture employed is predominately, i.e., 85–90 mole percent, the para isomer.

The petroleum sulfonic acid useful in the practice of this invention can be prepared from a deasphalted, solvent refined petroleum fraction having a viscosity of about 140 to 720 SUS at 210° F (99° C). A presently preferred sulfonation stock is a propane-fractionated, solvent extracted dewaxed Mid-Continent oil of about 200 to 230 SUS at 210° F (99° C) and having a viscosity index of about 90 to 100, or higher. A Mid-Continent oil is more precisely defined as a mixed base or intermediate base oil in "The Science of Petroleum", volume 1, page 7, Oxford University Press, London, Toronto and New York, 1938. Such oil is, for example, sulfonated with a 10 percent $SO_3$-90 percent $SO_2$ mixture in a continuous operation substantially as described in U.S. Pat. No. 3,135,693 to Whitney et al., using an $SO_3$ to oil weight ratio of about 0.08 and a reaction temperature of about 115° F (46° C). The total reaction time is about 5 minutes, including the mixing and soaking periods. The system is maintained in the liquid phase at a pressure of 100–120 psig (689–827 KPa). Effluent from the reaction unit is subjected to a two-stage flash for $SO_3$-$SO_2$ removal.

The diluents useful in the present invention include normally liquid saturated aliphatic, saturated cycloaliphatic or aromatic hydrocarbons, preferably boiling in the approximate range of 60° to 150° C, such as n-hexane, n-octane, cyclohexane, benzene, toluene, the xylenes, ethylbenzene, and the like; halogenated hydrocarbons such as chloroform and chlorobenzene; ethylene glycol ethers such as ethylene glycol monoethyl ether; and tetramethylene sulfone; and mixtures thereof. Presently preferred diluents are toluene and the xylenes.

The absorbent systems are prepared by refluxing a solution of the sulfonic acid in the inert diluent together with cuprous oxide, with provision for removing the water of reaction, such as a Dean-Stark Trap. The preparation is carried out in an oxygen-free atmosphere, such as under nitrogen, for a time sufficient to produce substantially complete reaction, using a molar ratio of sulfonic acid to copper of about 1.

It is desirable to have as much of the copper (I) salt in the absorbent system as possible consistent with ease of pumping; the higher the salt:diluent ratio, the greater will be in carbon monoxide complexing capacity of the system. Salt/diluent molarities of from 0.5 to 2 can provide satisfactory results.

The temperature at which the carbon monoxide is absorbed by the absorbent system is not critical. The absorption can be carried out at a temperature in the approximate range of 0° to about 10° C below the boiling point of the diluent. It is presently preferred to carry out the absorption step at a temperature in the approximate range of 20°–25° C below the boiling point of the diluent.

The absorption step can be carried out at any convenient pressure. Carbon monoxide partial pressures of 0.1 to 20 atmospheres can be employed, preferably between 1 and 10 atmospheres.

The carbon monoxide is separated from the carbon monoxide/absorbent complex by heating the mixture to a temperature in the approximate range of 10° C below the boiling point of the diluent to the boiling point of the diluent. It is presently preferred to carry out the desorption step at the boiling point of the diluent. The desorption step can be carried out at any convenient pressure. Absolute pressures in the range of 0.1 to 3 atmospheres, preferably from 0.5 to 2 atmospheres, can be employed.

In another embodiment of this invention, the methanation reaction is effected in the presence of a novel catalyst system which consists essentially of nickel on a calcium phosphate support which support has a Ca:P atomic ratio in the range of 1.4:1 to 2.3:1, promoted with barium or uranium. The catalyst and promoter metals may be in elemental form, oxides or mixtures.

The catalyst compositions employed in the present invention contain calcium, phosphorus, nickel and barium or uranium in the following amounts, expressed in terms of weight percent, based upon the weight of the total catalyst:

|  | Broad | Preferred |
| --- | --- | --- |
| Calcium | 5–35 | 10–25 |
| Phosphorus | 2–20 | 5–15 |
| Nickel | 10–50 | 20–40 |
| Barium | 1–20 | 2.5–18 |
| Uranium | 2–40 | 10–30 |

The difference between the sum of the percentages of the above-named elements and 100 percent is made up the oxygen content of the catalyst in amounts sufficient to satisfy the valence requirements of each of the elements in the catalyst.

In a presently preferred embodiment the support material has a Ca:P atomic ratio in the range of 1.5:1 to 1.8:1.

In a more preferred embodiment the support material has a Ca:P atomic ratio of 1.67:1 which corresponds to calcium hydroxyapatite, $Ca_5(OH)(PO_4)_3$.

These catalyst compositions are prepared by first preparing the calcium phosphate support by admixing an aqueous solution of a soluble calcium compound with an aqueous solution of a soluble phosphate compound.

Suitable calcium compounds include calcium acetate, calcium formate, calcium isobutyrate, calcium nitrate and the like. Suitable phosphorus compounds include ammonium and alkali metal phosphates.

In a presently preferred embodiment all the phosphorus is combined with the calcium, none of the phosphorus being available for combination with the nickel or the promoter metal.

The thus-prepared calcium phosphate gel is combined with suitable nickel and promoter metal compounds in a conventional manner, filtered, washed and dried. The dry catalyst material is then crushed, or otherwise reduced in size, then pilled or tableted and then calcined at a temperature in the range of 300° to 650° C for one-half to 10 hours, or more. Prior to use, the calcined material is reduced with hydrogen; alternatively, the dried catalyst material can be reduced with hydrogen at a temperature of 300° to 650° C without prior calcination.

The methanation reaction is carried out by contacting a mixture of carbon monoxide and steam with the above-described catalyst at an elevated temperature, according to the following reaction:

$$8\ CO + 16\ H_2O \rightarrow 6\ CO_2 + 2\ CH_4 + 12\ H_2O$$

The methanation reaction is conducted at a temperature in the approximate range of 300°–1000° F (148°–538° C), at a pressure in the approximate range of 0–2000 psig (0–13.7 MPa) at a gaseous hourly space velocity (GHSV) for carbon monoxide in the range of 100 to 10,000.

It is presently preferred that the methanation operation be conducted at a temperature in the approximate range of 400°–800° F (204°–427° C) and a pressure in the approximate range of 100 to 1,000 psig (0.689 to 6.89 MPa).

In yet another embodiment of the present invention, the nitrogen separated from the carbon monoxide in the carbon monoxide absorption zone is employed to provide mechanical energy by adiabatically expanding the nitrogen in an expansion motor. The cold nitrogen from the expansion motor can be employed to cool the several effluent streams.

Referring now to the drawing, char from a suitable source is introduced through line 2 to gasifier 104. An air/carbon dioxide mixture in line 4 is compressed in compressor 100. The compressed mixture is passed by line 6 through heat exchanger 102, where it is heated by heat exchange with the hot effluent gases from the gasifier 104, then introduced to gasifier 104. The gasification of the char is conducted at a temperature of about 2200° F (about 1204° C) and a pressure of about 300 psig (about 2.07 MPa).

The products of gasification comprising carbon monoxide, carbon dioxide and nitrogen, are withdrawn from the gasifier 104 through line 8 and passed through heat exchanger 102 wherein the gasifier effluent is partially cooled, giving up a portion of its heat to the incoming air/carbon dioxide mixture in line 6. Incombustible ash is withdrawn from gasifier 104 through line 10. The partially cooled effluent gas mixture in line 8 is then passed through heat exchanger 106 wherein the effluent mixture is further cooled.

The effluent gas mixture in line 8 is then passed to acid gas removal zone 108 wherein at least a portion of the carbon dioxide is removed from the gas mixture. As discussed previously, the char can contain up to about 4 weight percent sulfur. Should sulfur be present in the char, the effluent gas mixture in line 8 will also contain acidic sulfur-containing gases such as hydrogen sulfide and/or carbonyl sulfide. These sulfur-containing gases are removed from the gas stream in the removal zone 108.

The acid gases are removed in zone 108 by contacting the effluent gas mixture with a conventional material such as chilled methanol, hot aqueous potassium carbonate, mono- and diethanolamine and the like. The acid gas removal zone 108 can be of the conventional bubble-tray type, a packed column or any other liquid-gas contacting apparatus. Processes for the separation and recovery of these acid gases are well known in the art and will not be further discussed herein. The acid gases can be recovered from the acid removal zone 108 through line 10.

The effluent from the acid gas removal zone 108, consisting essentially of carbon monoxide and nitrogen, is passed through line 12 to carbon monoxide absorption zone 110 wherein the gas stream is contacted with an absorbent which is selective for absorbing carbon monoxide as previously described. The absorption zone 110 can be of the conventional bubble-tray type, a packed column or any other liquid-gas contacting apparatus.

Preferably, the carbon monoxide absorbent employed in absorption zone 110 is a 1M solution of copper (I) dodecylbenzenesulfonate in toluene. The absorption is effected at a temperature of about 20° C.

Line 14 at the top of absorption zone 110 permits removal of the nitrogen of reduced carbon monoxide content. Line 16 at the bottom of the absorption zone 110 conducts the carbon monoxide-enriched absorbent out of the absorption zone 110, through heat exchanger 112 to desorption zone 114.

In the desorption zone 114, the carbon monoxide-enriched absorbent is heated to about 110° C to liberate the carbon monoxide, which is withdrawn from the desorption zone 114 through line 18. The carbon monoxide-free absorbent is withdrawn from the desorption zone 114 through line 20, passed through the heat exchanger 112 and returned to the absorption zone 110. A side stream of the absorbent is passed to reboiler 116 wherein it is heated to about 110° C, then returned to the desorption zone 114.

The carbon monoxide in line 18 is passed through heat exchanger 118 to separator 120 wherein any absorbent diluent carried over in the carbon monoxide stream leaving the desorption zone 114 is separated from the carbon monoxide. The separated diluent is withdrawn from the separator 120 and returned to the desorption zone 114 through line 21. The carbon monoxide, now free of diluent, is withdrawn from the separator 120 through line 22 and passed to compressor 122 wherein the carbon monoxide is compressed to about 150 psig (about 1.03 MPa). The compressed carbon monoxide is withdrawn from compressor 122 through line 24 and passed through heat exchanger 124 wherein it is cooled to about 120° F (about 49° C) with cooling water, then through heat exchanger 126 wherein it is cooled to about −40° F (about −40° C) with cold nitrogen from line 28 hereinafter explained.

The nitrogen in line 14, withdrawn from absorption zone 110, is passed to expansion motor 128. As the nitrogen passes through the absorption zone 110, it can carry over a small amount of the absorbent diluent, in the gaseous form. The diluent/nitrogen gases in line 14 are explained in the turbo or reciprocating expansion motor 128 under substantially adiabatic conditions. The resultant gas mixture has a temperature of about −40° F and a pressure of about atmospheric which causes the diluent substantially to condense. The cold gas/diluent mixture flows from the expansion motor 128 through line 26 to separator 130 where an overhead nitrogen stream is removed through line 28 and a liquid diluent can be returned to desorption zone 114 through line 30.

The expansion motor 128 can be direct coupled to the compressor 122, or it can be connected to an electrical generator 132, to provide electrical energy.

The cold nitrogen in line 28 is used to cool the compressed carbon monoxide in heat exchanger 126. Cool nitrogen is withdrawn form the heat exchanger 126 through line 31 for later use. The cooled, compressed carbon monoxide is withdrawn from heat exchanger 126 through line 32 and passed to separator 133 wherein any residual, condensed diluent is separated from the carbon monoxide. A liquid diluent stream is withdrawn from separator 133 through line 34 and returned to desorption zone 114.

An overhead carbon monoxide stream is withdrawn from separator 133 through line 36 and passed to heat exchanger 134 wherein the carbon monoxide is heated to about 400° F (about 204° C). Steam, through line 38, is combined with the carbon monoxide and the combined stream is passed to methanation reactor 136.

Within the methanation reactor 136 the steam/carbon monoxide mixture is contacted with a nickel catalyst on a calcium phosphate support at a temperature of about 600°–700° F (about 316°–371° C) at a pressure of about 150 psig (about 1.03 MPa). Since the reaction is exothermic, cooling water is supplied to cooling coils 138 through line 40. The steam generated in the coils 138 is withdrawn through line 42 and can be used to supply at least a portion of the heat requirements elsewhere in the process, as required. The methanation reactor 136 is preferably a fluidized bed reactor, but can be of any configuration normally used for this type reaction.

The effluent from the methanation reactor, consisting essentially of a mixture of methane, carbon dioxide, hydrogen and steam is passed through line 44 to heat exchanger 138 where it is cooled to about 160°–200° F (about 71°–93° C) with cooling water, causing the steam to condense. The mixed stream is then passed to separator 140 wherein the water is separated from the gas mixture. The separated water is withdrawn from separator 140 through line 45. The substantially water-free gas mixture is withdrawn from separator 140 through line 46 and passed to carbon dioxide removal and recovery zone 142 wherein the carbon dioxide is removed by contacting the gas stream with an absorbent which is selective for carbon dioxide. The carbon dioxide removal and recovery zone 142 can be any conventional liquid-gas contacting apparatus such as a bubble-tray tower or a packed column. The carbon dioxide absorbent can be any conventional carbon dioxide absorbent material, such as hot aqueous potassium carbonate.

The carbon dioxide-free effluent from the removal and recovery zone 142, consisting essentially of methane and hydrogen is passed by way of line 48 through heat exchanger 144 wherein it is cooled and partially dried with cool nitrogen in line 31. The product gas is withdrawn from the heat exchanger 144 through line 50. The product gas can be further treated to remove any residual moisture such as by contact with propylene glycol, after which it is suitable for use in admixture with or in place of natural gas.

The carbon dioxide recovered in the carbon dioxide removal and recovery zone 142 is withdrawn through line 52. At least a portion of the carbon dioxide in line 52 is passed to the first step of the process through line 54 to line 4 where it is combined with air. Excess carbon dioxide is passed through line 55 to further processing or disposal, not shown.

The product gas is calculated to contain 88.6 mole percent methane, 10.4 mole percent hydrogen and 1 mole percent carbon dioxide. It is calculated to have a calorific value of 920 BTU/SCF (about 34.3 kJ/m$^3$, a Wobbe number of 1280 and a Weaver flame speed of 19 cm/sec.).

Reasonable variations and modifications, which will be apparent to those skilled in the art, can be made in this invention without departing from the spirit and scope thereof.

What is claimed is:

1. A process for the production of a gas comprising methane which comprises, in combination, the steps of
   a. gasifying a solid carbonaceous material at an elevated temperature in the presence of air and carbon dioxide to produce a raw process stream comprising carbon monoxide, carbon dioxide and nitrogen;
   b. cooling, cleaning and purifying said raw process stream to obtain a stream consisting essentially of carbon monoxide and nitrogen;
   c. separating carbon monoxide from said stream consisting essentially of carbon monoxide and nitrogen by contacting said stream in an absorption zone with an absorbent consisting essentially of an inert hydrocarbon diluent and at least one copper sulfonate, wherein said carbon monoxide is taken up in said absorbent, withdrawing from said absorption zone a stream consisting essentially of nitrogen and a stream consisting essentially of said absorbent and said carbon monoxide, passing said stream consisting essentially of absorbent and carbon monoxide to a desorption zone, separating in said desorption zone said carbon monoxide from said absorbent and withdrawing said carbon monoxide from said desorption zone;
   d. combining stream with said separated carbon monoxide and reacting the resulting CO/steam mixture in a catalytic methanation zone to produce an effluent gas stream consisting essentially of carbon dioxide, methane and hydrogen; and
   e. cooling said effluent gas stream and separating impurities therefrom to produce a product stream comprising methane.

2. The process of claim 1 wherein said copper sulfonate is the copper (I) salt of an organic sulfonic acid selected from the group consisting of:
   a. alkane sulfonic acids having from 4 to 6 carbon atoms per molecule,
   b. aromatic sulfonic acids having from 6 to 22 carbon atoms per molecule, and
   c. petroleum sulfonic acids.

3. The process of claim 2 wherein said salt is copper (I) dodecylbenzenesulfonate.

4. The process of claim 2 wherein said salt is copper (I) 2-ethylhexanesulfonate.

5. The process of claim 1 wherein said nitrogen is passed to an expansion motor wherein said nitrogen is adiabatically expanded to provide mechanical energy.

6. A process for the production of a gas comprising methane which comprises, in combination, the steps of
   a. gasifying a solid carbonaceous material at an elevated temperature in the presence of air and carbon dioxide to produce a raw process stream comprising carbon monoxide, carbon dioxide and nitrogen;
   b. cooling, cleaning and purifying said raw process stream to obtain a stream consisting essentially of carbon monoxide and nitrogen;
   c. separating carbon monoxide from said stream consisting essentially of carbon monoxide and nitrogen;
   d. combining steam with the separated carbon monoxide and reacting the resulting CO/steam mixture in a catalytic methanation zone by contacting said mixture with a methanation catalyst consisting essentially of nickel, a promoter selected from the group consisting of barium and uranium, and a calcium phosphate support having a Ca:P atomic ratio in the range of 1.4:1 to 2.3:1, wherein the components are present in approximate amounts as follows:

| Calcium | 5 to 35, | |
|---|---|---|
| Phosphorus | 2 to 20, | |
| Nickel | 10 to 50 | and either |
| Barium | 1 to 20, | or |
| Uranium | 2 to 40, | | all said amounts expressed in terms of weight percent, based upon the weight of the total catalyst, thereby producing an effluent gas stream consisting essentially of carbon dioxide, methane and hydrogen; and e. cooling said effluent gas stream and separating impurities therefrom to produce a product stream comprising methane.

7. The process of claim 6 wherein said Ca:P ratio is in the range of 1.5:1 to 1.8:1.

8. The process of claim 6 wherein said Ca:P ratio is about 1.67:1.

9. The process of claim 6 wherein said components are present in the following approximate amounts:

| Calcium | 10 to 25, | |
|---|---|---|
| Phosphorus | 5 to 15, | |
| Nickel | 20 to 40, | |
| Barium | 2.5 to 18 | and |
| Uranium | 10 to 30. | |

10. The process of claim 6 wherein said catalyst promoter is barium.

11. The process of claim 6 wherein said catalyst promoter is uranium.

12. A process for the production of a gas comprising methane which comprises, in combination, the steps of a. gasifying a solid carbonaceous material at an elevated temperature in the presence of air and carbon dioxide to produce a raw process stream comprising carbon monoxide, carbon dioxide and nitrogen;

b. cooling, cleaning and purifying said raw process stream to obtain a stream consisting essentially of carbon monoxide and nitrogen;

c. separating carbon monoxide from said stream consisting essentially of carbon monoxide and nitrogen by contacting said stream in an absorption zone with an absorbent consisting essentially of an inert hydrocarbon diluent and at least one copper sulfonate, wherein said carbon monoxide is taken up in said absorbent, withdrawing from said absorption zone a stream consisting essentially of nitrogen and a stream consisting essentially of said absorbent and said carbon monoxide, passing said stream consisting essentially of absorbent and carbon monoxide to a desorption zone, separation in said desorption zone said carbon monoxide from said absorbent and withdrawing said carbon monoxide from said desorption zone;

d. combining steam with the separated carbon monoxide and reacting the resulting CO/steam mixture in a catalytic methanation zone by contacting said mixture with a methanation catalyst consisting essentially of nickel, a promoter selected from the group consisting of barium and uranium, and a calcium phosphate support having a Ca:P atomic ratio in the range of 1.4:1 to 2.3:1, wherein the components are present in approximate amounts as follows:

| Calcium | 5 to 35, | |
|---|---|---|
| Phosphorus | 2 to 20, | |
| Nickel | 10 to 50, | and either |
| Barium | 1 to 20, | or |
| Uranium | 2 to 40, | | all said amounts expressed in terms of weight percent, based upon the weight of the total catalyst, thereby producing an effluent gas stream consisting essentially of carbon dioxide, methane and hydrogen; and e. cooling said effluent gas stream and separating impurities therefrom to produce a product stream comprising methane.

13. The process of claim 12 wherein said copper sulfonate is the copper (I) salt of organic sulfonic acid selected from the group consisting of:

a. alkane sulfonic acid having from 4 to 6 carbon atoms per molecule, b. aromatic sulfonic acids having from 6 to 22 carbon atoms per molecule, and c. petroleum sulfonic acids.

14. The process of claim 13 wherein said salt is copper (I) dodecylbenzenesulfonate.

15. The process of claim 13 wherein said salt is copper (I) 2-ethylhexanesulfonate.

16. The process of claim 12 wherein said nitrogen is passed to an expansion motor wherein said nitrogen is adiabatically expanded to provide mechanical energy.

17. The process of claim 12 wherein said Ca:P ratio is in the range of 1.5:1 to 1.8:1.

18. The process of claim 12 wherein said Ca:P ratio is about 1.67:1.

19. The process of claim 12 wherein said components are present in the following approximate amounts:

| Calcium | 10 to 25, | |
|---|---|---|
| Phosphorus | 5 to 15, | |
| Nickel | 20 to 40, | |
| Barium | 2.5 to 18, | and |
| Uranium | 10 to 30. | |

20. The process of claim 12 wherein said catalyst promoter is barium.

21. The process of claim 12 wherein said catalyst promoter is uranium.

* * * * *

UNITED STATES PATENT AND TRADEMARK OFFICE
CERTIFICATE OF CORRECTION

PATENT NO. : 4,011,058
DATED : March 8, 1977
INVENTOR(S) : Marvin M. Johnson et al It is certified that error appears in the above-identified patent and that said Letters Patent are hereby corrected as shown below:

Column 8, line 42, "4 to 6" should read --4 to 20--.

Column 10, line 1, "separation" should read --- separating ---.

Column 10, line 31, after "of" and before "organic" insert --- an ---.

Column 10, line 33, "acid" should read --- acids ---.

Column 10, line 33, "4 to 6" should read --4 to 20 --.

Signed and Sealed this

Thirteenth Day of June 1978

[SEAL]

Attest:

RUTH C. MASON
Attesting Officer

DONALD W. BANNER
Commissioner of Patents and Trademarks